US011061037B2

(12) United States Patent
Rouet et al.

(10) Patent No.: US 11,061,037 B2
(45) Date of Patent: Jul. 13, 2021

(54) DIAGNOSTIC OF HEART FAILURE

(71) Applicants: INSERM (Institut National de la Sante et de la Recherche Medicale), Paris (FR); Universite Paul Sabatier Toulouse III, Toulouse (FR); Centre Hospitalier Universitaire de Toulouse, Toulouse (FR)

(72) Inventors: Philippe Rouet, Toulouse (FR); Fatima Smih-Rouet, Toulouse (FR); Franck Desmoulin, Toulouse (FR); Michel Galinier, Toulouse (FR)

(73) Assignees: INSERM (INSTITUT DE LA SANTE ET DE LA RECHERCHE MEDICALE), Paris (FR); UNIVERSITE PAUL SABATIER TOULOUSE III, Toulouse (FR); CENTRE HOSPITALIER UNIVERSITAIRE DE TOULOUSE, Toulouse (FR)

( * ) Notice: Subject to any disclaimer, the term of this patent is extended or adjusted under 35 U.S.C. 154(b) by 209 days.

(21) Appl. No.: 15/869,438

(22) Filed: Jan. 12, 2018

(65) Prior Publication Data

US 2018/0143208 A1    May 24, 2018

Related U.S. Application Data

(63) Continuation of application No. 14/419,566, filed as application No. PCT/EP2013/066697 on Aug. 9, 2013, now abandoned.

(30) Foreign Application Priority Data

Aug. 9, 2012 (EP) .................... 12305988

(51) Int. Cl.
G01N 33/53      (2006.01)
G01N 33/68      (2006.01)
G01N 27/447     (2006.01)

(52) U.S. Cl.
CPC ....... G01N 33/6893 (2013.01); G01N 27/447 (2013.01); G01N 33/6848 (2013.01); G01N 27/4473 (2013.01); G01N 2333/4745 (2013.01); G01N 2800/325 (2013.01); G01N 2800/50 (2013.01)

(58) Field of Classification Search
None
See application file for complete search history.

(56) References Cited

U.S. PATENT DOCUMENTS

| 2006/0183681 A1* | 8/2006 | Ebrahim | G01N 33/74 514/2.3 |
| 2006/0188504 A1* | 8/2006 | Node | G01N 33/6869 424/145.1 |
| 2011/0144205 A1 | 6/2011 | Damy et al. | |
| 2014/0065648 A1* | 3/2014 | Wienhues-Thelen | G01N 33/6887 435/7.94 |
| 2014/0206632 A1* | 7/2014 | Todd | G01N 33/6869 514/26 |
| 2015/0119269 A1 | 4/2015 | McPherson et al. | |

FOREIGN PATENT DOCUMENTS

| JP | 2010517023 A | 5/2010 |
| WO | 2006120152 | 11/2006 |
| WO | 2008005469 | 1/2008 |
| WO | 2012006681 | 1/2012 |

OTHER PUBLICATIONS

Hassfeld et al., "Insulin-Like Growth Factor-Binding Proteins 2 and 3 are Independent Predictors of a Poor Prognosis in Patients with Dilated Cardiomyopathy", Heart, Mar. 1, 2007, vol. 93, No. 3, p. 359-360.
Stastna et al., "Secreted Proteins as a Fundamental Source for Biomarker Discovery" Proteomics, Jan. 19, 2012, vol. 12, No. 4-5, p. 722-735.
Hu et al., "Serum Insulin-Like Growth Factor-1 Binding Proteins 1 and 2 and Mortality in Older Adults: The Health, Aging, and Body Composition Study", JAGS, Jun. 18, 2009, vol. 57, p. 1213-12118.
Olchovsky et al., "Elevated Insulin-Like Growth Factor-1 and Insulin-Like Growth Factor Binding Protein-2 in Malignant Pleural Effusion", Acta Oncologica, Jan. 1, 2002, vol. 42, No. 2, p. 182-187.
Yu et al., "Insulin-Like Growth Factors ( IGF-I, Free IGF-I, and IGF-II) and Insulin-Like Growth Factor Binding Proteins (IGFBP-2, IGFBP-3, IGFBP-6, and ALS) in Blood Circulation", Journal of Clinical Laboratory Analysis, Jan. 1, 1999, vol. 12, p. 166-172.
Mattsson et al., "Multidimensional Reference Regions for IGF-1, IGFBP-2 and IGFBP-3 Concentrations in Serum of Healthy Adults", Growth Hormone and IGF Research, Dec. 1, 2008, vol. 18, No. 6, p. 506-516.
Mischak et al., "Comprehensive human urine standards for comparability and standardization in clinical proteome analysis", Proteomics Coin Appl. Apr. 2010; 4(4), pp. 464-478.

* cited by examiner

*Primary Examiner* — Gary Counts
(74) *Attorney, Agent, or Firm* — W&C IP

(57) ABSTRACT

Disclosed herein is a method for classifying a patient at risk for heart failure, wherein the method comprises the steps of (i) measuring the concentration of IGFBP2 in a sample obtained from the patient and (ii) comparing the concentration of IGFBP2 measured in step (i) to a control value derived from the concentration of IGFBP2 in samples from patients who are at particular stages of heart failure and/or to a control value derived from the concentration of IGFBP2 in blood samples from healthy patients.

8 Claims, 10 Drawing Sheets

Figure 1:
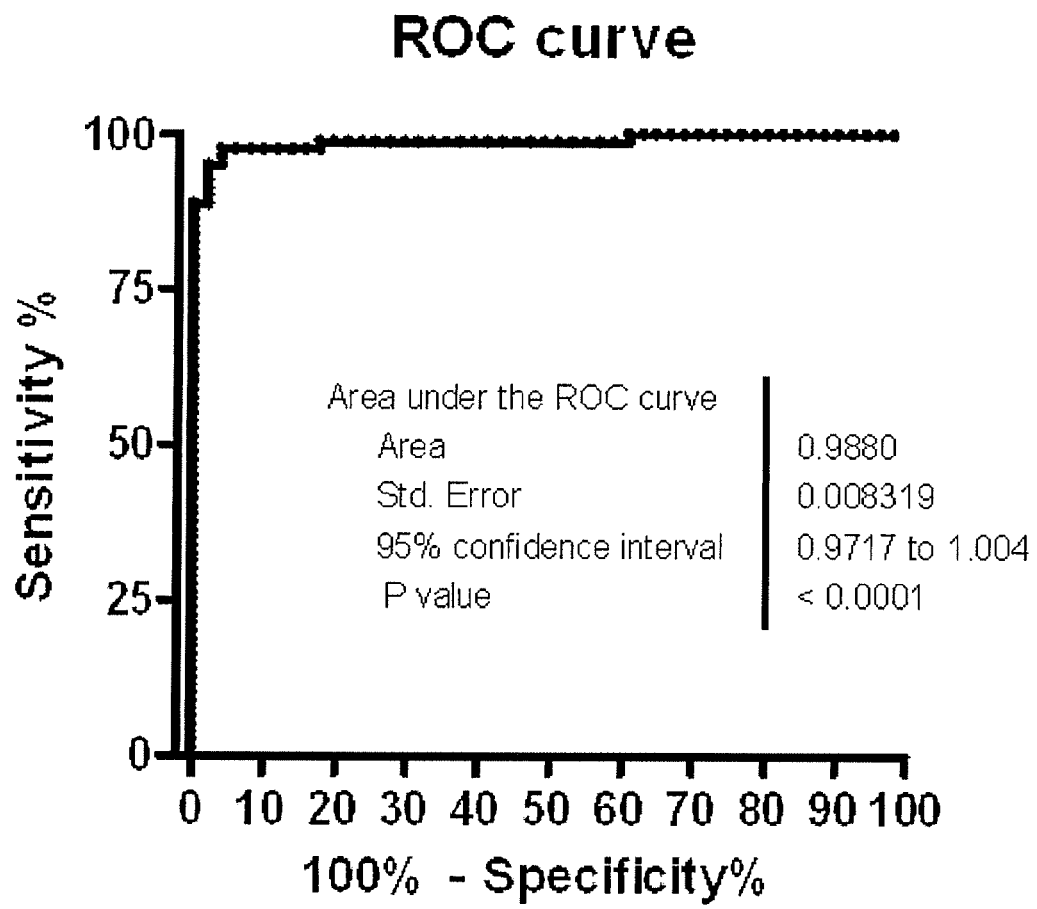

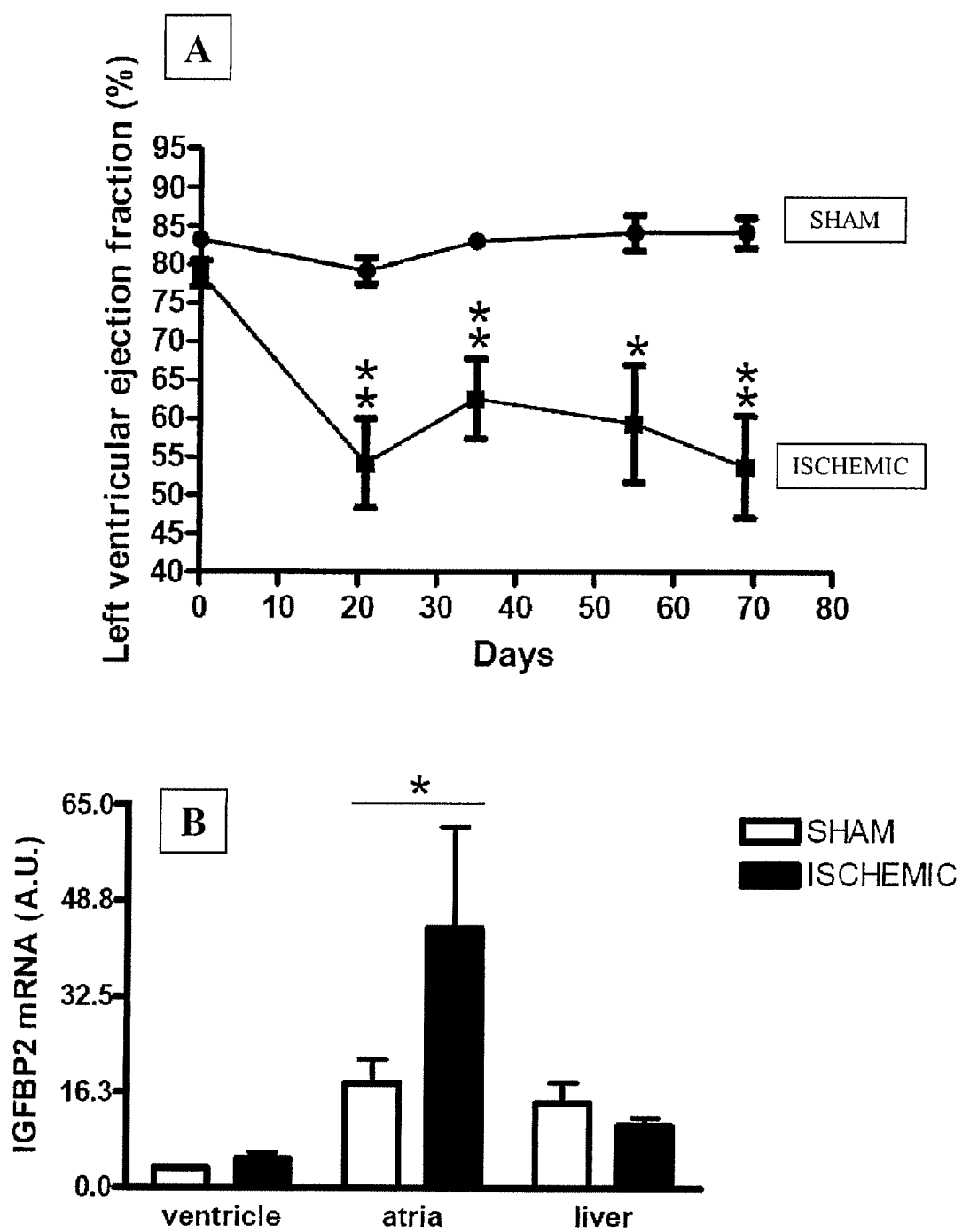
Figure 10 A and B

DIAGNOSTIC OF HEART FAILURE

CROSS REFERENCE TO RELATED APPLICATIONS

This application is a continuation of U.S. application Ser. No. 14/419,566 filed Feb. 2, 2015, now abandoned which is a National Stage Application based on the International Application No. PCT/EP2013/066697 filed Aug. 9, 2013 which claims priority to European Application 12305988.3 filed Aug. 9, 2012.

FIELD OF THE INVENTION

The invention relates to a method for classifying a patient at risk for heart failure, wherein said method comprises the steps of (i) measuring the concentration of IGFBP2 in a sample obtained from said patient and (ii) comparing the concentration of IGFBP2 measured in step (i) to a control value derived from the concentration of IGFBP2 in samples from patients who are at particular stages of heart failure and/or to a control value derived from the concentration of IGFBP2 in blood samples from healthy patients.

BACKGROUND OF THE INVENTION

Prevalence of heart failure (HF) is growing because of the ageing and the cardiovascular risk factors in general population [Delahaye, F. et al., 2001]. The HF diagnosis remains too often complicated because of atypical presentation and the need to specialized care access. To help clinicians diagnose heart failure, blood HF biomarkers have been proposed, such as the natriuretic peptides (NP). However, NP have limitations which sustains a need for more specific and more accurate biomarkers that would allow for facilitated large scale HF screenings. In addition, 30% of the patients admitted to emergency care for acute dyspnea have a brain natriuretic peptides (BNP) concentration in a «gray zone» that does not allow for diagnosis. In these cases, HF diagnosis will require costly and time consuming examinations. However, it is recognized that a rapid diagnosis and early medical care of the patient have a positive impact on the patient's health and also lower the cost of the treatment.

The article Hassfeld S. et al 2007 discloses the use of IGFBP2 as a biomarker for the prognostic of patients with dilated cardiomyopathy who represents an etiological subset of HF patients and doesn't disclose the use of the IGFBP2 for the diagnostic of heart failure.

SUMMARY OF THE INVENTION

The inventors have launched a prospective monocentric case-control study and investigated for urinary polypeptides specific to acute (AHF) or chronic heart failure (CHF) with holistic analytical strategy by using the capillary electrophoresis-mass spectroscopy technique (CE-MS). They find that IGFBP2 concentration may be used as a biomarker of heart failure as a biomarker to classify patients with heart failure.

Thus, the invention relates to a method for classifying a patient at risk for heart failure, wherein said method comprises the steps of (i) measuring the concentration of IGFBP2 in a sample obtained from said patient and (ii) comparing the concentration of IGFBP2 measured in step (i) to a control value derived from the concentration of IGFBP2 in samples from patients who are at particular stages of heart failure and/or to a control value derived from the concentration of IGFBP2 in blood samples from healthy patients.

DETAILED DESCRIPTION OF THE INVENTION

Classification and Diagnostic Method

The invention relates to a method for classifying a patient at risk for heart failure, wherein said method comprises measuring the concentration of IGFBP2 in a sample obtained from said patient.

In a particular embodiment, said method further comprises the steps of:

(i) measuring the concentration of IGFBP2 in a sample obtained from said patient, (ii) comparing the concentration of IGFBP2 measured in step (i) to a threshold value derived from the concentration of IGFBP2 in samples from patients who are at particular stages of heart failure and/or to a threshold value derived from the concentration of IGFBP2 in samples from healthy patients.

The invention also relates to a method for diagnosis of heart failure in a patient comprising the steps consisting of i) determining the concentration of IGFBP2 in a sample obtained from said patient; and ii) comparing said concentration to a control value.

In a particular embodiment, the patient has significant comorbid conditions, including hypertension, coronary heart disease and diabetes for example diabetes mellitus.

In another particular embodiment, the patient is on diuretics or antiplatelet agents.

In another particular embodiment, the patient is more than 50 years old. In another particular embodiment, the patient is more than 60 years old.

In one embodiment, the heart failure may be an asymptomatic heart failure, a chronic heart failure or an acute heart failure.

Typically, the sample according to the invention may be a blood, plasma, serum, lymph, urine sample, cardiac tissues like atria or ventricle or liver. In a particular embodiment, said sample is plasma or urine.

As used herein, the term "IGFBP2" for "Insulin-like Growth Factor-Binding Protein 2" denotes a protein which serves as a carrier protein for Insulin-like growth factor 1 (IGF I) or Insulin-like growth factor 2 (IGF II). As used herein, the term "IGFBP2" denotes also fragments of IGFBP2. As used herein, the term "fragments of IGFBP2" denotes shorter peptides becoming from chemical or biochemical hydrolysis of IGFBP2.

Thus, in a particular embodiment, the invention relates a method for classifying a patient at risk for heart failure or to a method for diagnosis of heart failure in a patient according to the patient by determining the concentration of fragments of IGFBP2.

As used herein, the term "heart failure" denotes inability of the heart to supply sufficient blood flow to meet the body's needs and this pathology is well-described in medicine practice. This term encompasses chronic heart failure, acute heart failure, myocardial infarction, unstable angina, diastolic dysfunction, systolic dysfunction and diabetic cardiomyopathy.

As used herein, the term "chronic heart failure" denotes a long term situation, usually with stable treated symptomatology.

As used herein, the term "acute heart failure" denotes to sudden onset heart failure, as well as acute "exacerbated" or "decompensated" heart failure, referring to episodes in which a patient with known chronic heart failure or devoid of chronic heart failure abruptly develops worsening symptoms and requires hospitalization. Common symptoms of complications due to acute heart failure include, but are not limited to, dyspnea due to pulmonary congestion or cardiogenic shock due to low cardiac output, easy fatigueability (exercise intolerance), peripheral edema, anasarca (pronounced generalized edema), nocturia (frequent nighttime urination), bradycardia, heart block, hypotension, dizziness, syncope, diabetes, oliguria or anuria, hypokalemia, bronchospasm, cold sweat, and asthma.

A patient with a heart failure is classified according to an international gradation namely the New York Heart Association (NYHA) functional classification. Functional classification of heart failure is generally done by the New York Heart Association Functional Classification (Criteria Committee, New York Heart Association. Diseases of the heart and blood vessels). Nomenclature and criteria for diagnosis, 6th ed. Boston: Little, Brown and co, 1964; 114). This classification stages the severity of heart failure into 4 classes (I-IV).

A patient with cardiac disease but resulting in no limitation of physical activity is classified as a NYHA class I. Ordinary physical activity does not cause undue fatigue, palpitation, dyspnea or anginal pain. A asymptomatic patient is classified as a NYHA class I.

A patient with cardiac disease resulting in slight limitation of physical activity is classified as a NYHA class II. Ordinary physical activity results in fatigue, palpitation, dyspnea or anginal pain. They are comfortable at rest.

A patient with cardiac disease resulting in marked limitation of physical activity is classified as a NYHA class III. Less than ordinary activity causes fatigue, palpitation, dyspnea or anginal pain. They are comfortable at rest.

A patient with cardiac disease resulting in inability to carry on any physical activity without discomfort is classified as a NYHA class IV. Symptoms of cardiac insufficiency or of the anginal syndrome may be present even at rest. If any physical activity is undertaken, discomfort is increased.

According to the method for classifying a patient at risk for heart failure, more a patient will have a high concentration of IGFBP2, more his heart failure will be severe.

For example and according to thresholds value determined by the inventors, a patient with a high concentration of IGFBP2, for example more than 1300 ng/ml in plasma, will be classified as having an heart failure of class IV.

The term "detecting" or "determining" as used above includes qualitative and/or quantitative detection (measuring levels) with or without reference to a control. Typically IGFBP2 concentrations may be measured for example by capillary electrophoresis-mass spectroscopy technique (CE-MS) or ELISA performed on the sample.

Preferably, the invention relates to a method for diagnosis of heart failure in a patient comprising a step a) consisting of measuring IGFBP2 concentration in a sample obtained from said patient. Preferably, the method of the invention further comprises a step of comparing the concentration of IGFBP2 obtained in step a) to a threshold level.

The "control" may be a healthy subject, i.e. a subject who does not suffer from any heart failure. The control may also be a subject suffering from heart failure. Preferably, said control is a healthy subject.

Detection of IGFBP2 concentration in the sample may also be performed by measuring the level of IGFBP2 protein. In the present application, the "level of IGFBP2 protein" means the quantity or concentration of said IGFBP2 protein. In another embodiment, the "level of IGFBP2" means the level of IGFBP2 fragments.

Such methods comprise contacting a sample with a binding partner capable of selectively interacting with IGFBP2 protein peptides present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, capillary electrophoresis-mass spectroscopy technique (CE-MS). etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against the proteins to be tested. A sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule is added. The secondary binding molecule is allowed to react with any captured sample marker protein, the plate is washed and the presence of the secondary binding molecule is detected using methods well known in the art.

Methods of the invention may comprise a step consisting of comparing IGFBP2 protein and fragments concentration in circulating cells with a control value. As used herein, "concentration of IGFBP2" refers to an amount or a concentration of a transcription product, for instance the protein IGFBP2. Typically, a level of a protein can be expressed as nanograms per microgram of tissue or nanograms per milliliter of a culture medium, for example. Alternatively, relative units can be employed to describe a concentration. In a particular embodiment, "concentration of IGFBP2" may refer to fragments of IGBP2. Thus, in a particular embodiment, fragments of IGFBP2 may also be measured.

In one embodiment, the invention relates to a method for classifying a patient at risk for heart failure, wherein said method comprises measuring the concentration of IGFBP2 in a sample obtained from said patient. As already explained, more a patient will have a high concentration of IGFBP2, more his heart failure will be severe.

The inventors have established threshold values which are able to classifying patient with heart failure.

When the measure of IGFBP2 concentration is performed by Elisa method in plasma, a patient with a concentration of IGFBP2 with less than 600 ng/ml, preferably less than 500 ng/ml, even preferably less than 400 ng/ml most preferably less than 300 ng/ml is indicative of a heart failure of stage I according to the NYHA heart failure classification.

When the measure of IGFBP2 concentration is performed Elisa method in plasma, a patient with a concentration of IGFBP2 comprised between about 600 ng/ml and about 1100 ng/ml, preferably between about 800 ng/ml and about 1050 ng/ml, preferably between about 900 ng/ml and about 1000 ng/ml, most preferably between about 925 ng/ml and about 975 ng/ml is indicative of a heart failure of stage II according to the NYHA heart failure classification.

When the measure of IGFBP2 concentration is performed Elisa method in plasma, a patient with a concentration of IGFBP2 comprised between about 1100 ng/ml and about 1300 ng/ml, preferably between about 1150 ng/ml and about 1250 ng/ml, most preferably between about 1175 ng/ml and about 1225 ng/ml is indicative of a heart failure of stage III according to the NYHA heart failure classification.

When the measure of IGFBP2 concentration is performed by Elisa method is performed by capillary electrophoresis-mass spectroscopy technique (CE-MS) in plasma, a patient with a concentration of IGFBP2 more than 1300 ng/ml, preferably more than 1350 ng/ml, even preferably more than 1400 ng/ml, most preferably more than 1450 ng/ml is indicative of a heart failure of stage IV according to the NYHA heart failure classification.

In another embodiment, the invention relates to a method for diagnosis heart failure in a patient comprising determining the concentration of IGFBP2 in a sample obtained from said patient and comparing said concentration to a threshold value.

When the measure of IGFBP2 protein or is performed by Elisa method the level of IGFBP2 in a patient suffering of heart failure is increased by at least 50%, preferably by at least 70%, preferably by at least 100%; preferably by at least 150%, preferably by at least 200%, preferably by at least 250%, more preferably by at least 300%, even more at least 400% compared to a control reference. In other words, preferably, when IGFBP2 protein is measured by Elisa method, the quantity of IGFBP2 protein in a patient suffering of heart failure is increased by at least 50%, preferably by at least 70%, preferably by at least 100%; preferably by at least 150%, preferably by at least 200%, preferably by at least 250%, more preferably by at least 300%, even more at least 400% compared to a control reference.

Concentration of IGFBP2 in plasma has been measured by Elisa technique. The inventors have established a threshold value for concentration of IGFBP2 to easily diagnose heart failure. Preferably, this threshold value is more than 150 ng/ml, preferably more than 200 ng/ml, even most preferable more than 250 ng/ml, most preferably said threshold value is more than 300 ng/ml.

Concentration of IGFBP2 in urine has been measured by Elisa technique in urine. The inventors have established a threshold value for concentration of IGFBP2 to easily diagnose heart failure. Preferably, this threshold value is more than 2.5 ng/ml, most preferably said threshold value is more than 3 ng/ml.

Typically, a "threshold value", "threshold level" or "cut-off value" can be determined experimentally, empirically, or theoretically. A threshold value can also be arbitrarily selected based upon the existing experimental and/or clinical conditions, as would be recognized by a person of ordinary skilled in the art. Preferably, the person skilled in the art may compare the concentration of IGFBP2 obtained according to the method of the invention with a defined threshold value.

Preferably, said threshold value is the mean concentration of IGFBP2 of a population of healthy individuals. As used herein, the term "healthy individual" denotes a human which is known to be healthy, i.e. which does not suffer from heart failure, has never been subjected to such chronic heart failure, and does not need any medical care.

Preferably, said threshold value is the mean concentration of IGFBP2 of a population of sick individuals. As used herein, the term "sick individual" denotes a human which is known to be sick, i.e. which suffers from heart failure at any stage of heart failure as according to the NYHA heart failure classification.

Typically, the skilled person in the art may determine the concentration of IGFBP2 in a biological sample, preferably plasma or urine, of 100 individuals known to be healthy or sick. The mean value of the obtained concentrations is then determined, according to well known statistical analysis, so as to obtain the mean concentration of IGFBP2. Said value is then considered as being normal and thus constitute a threshold value. By comparing the concentrations of IGFBP2 to this threshold value, the physician is then able to diagnose heart failure or classifying patients. Indeed, by comparing the concentrations of IGFBP2 obtained in a biological sample, preferably plasma or urine, of a given subject to a threshold value, one can easily determine whether said subject suffers from heart failure or not or can easily determine the stage of the heart failure according to the NYHA heart failure classification.

Accordingly, the physician would be able to adapt and optimize appropriate medical care of a subject in a critical and life-threatening condition suffering from heart failure. The determination of said prognosis is highly appropriate for follow-up care and clinical decision making.

Therefore, the invention is drawn to a method for diagnosis of heart failure in a patient or for classifying a patient at risk for heart failure comprising the following steps:
 a) determining the concentration of IGFBP2 in a sample obtained from said patient;
 b) determining the mean concentration of IGFBP2 in a biological sample of a population of healthy or sick individuals, preferably 100 healthy individuals; and
 c) a step of comparing the concentration of IGFBP2 obtained of a) to the mean concentration of IGFBP2 obtained in b).

In a further embodiment of the invention, methods of the invention comprise measuring the concentration of at least one further biomarker.

The term "biomarker", as used herein, refers generally to a molecule, the expression of which in a sample from a patient can be detected by standard methods in the art (as well as those disclosed herein), and is predictive or denotes a condition of the subject from which it was obtained.

For example, the other biomarker may be selected from the group of heart failure biomarkers consisting of brain natriuretic peptide (BNP), amino-terminal pro-brain natriuretic peptide (NT-pro BNP), norepinephrine, troponin, heart-type fatty acid binding protein, myosin light chain-1, matrix metalloproteinase, tissue inhibitor of matrix metalloproteinase, C-reactive protein (CRP), TNFalpha, soluble tumor necrosis factor receptor 1 (sTNFR1), soluble TNFR2 receptor, soluble IL-2 receptor, CD40-CD154, CCAM-I, P-selectin, tissue factor and von Willebrand factor, urocortin, myeloperoxidase, and uric acid.

In a preferred embodiment, the further biomarker of heart failure is BNP or NT-pro BNP.

Yet another object of the invention relates to a kit for performing a method of the invention, said kit comprising means for measuring the concentration of IGFBP2 in a sample obtained from a patient. The kit may include an antibody, or a set of antibodies as above described. In a particular embodiment, the antibody or set of antibodies are labelled as above described. The kit may also contain other suitably packaged reagents and materials needed for the particular detection protocol, including solid-phase matrices, if applicable, and standards. The kit may also contain one or more means for the detection of a further biomarker. Typically the kit may also contain means for the detection of one or more heart failure biomarker selected from the group consisting of brain natriuretic peptide (BNP), amino-terminal pro-brain natriuretic peptide (NT-pro BNP), norepinephrine, troponin, heart-type fatty acid binding protein, myosin light chain-1, matrix metalloproteinase, tissue inhibitor of matrix metalloproteinase, C-reactive protein (CRP), TNFalpha, soluble tumor necrosis factor receptor 1 (sTNFR1), soluble T2 receptor, soluble IL-2 receptor, CD40-CD154, CCAM-I, P-selectin, tissue factor and von Willebrand factor, urocortin, myeloperoxidase, galectin-3 and uric acid.

In a one embodiment, kit of the invention comprises means for measuring the concentration of IGFBP2 and means for measuring the concentration of BNP or NT-pro BNP.

A further object of the invention relates to the use of IGFBP2 as a biomarker for heart failure.

The invention will be further illustrated by the following figures and examples. However, these examples and figures should not be interpreted in any way as limiting the scope of the present invention.

FIGURES

FIG. 1: ROC curve analysis of IGFBP2 levels from CHF and AHF patients (n=80) vs control subjects (n=50).

Figure 2:
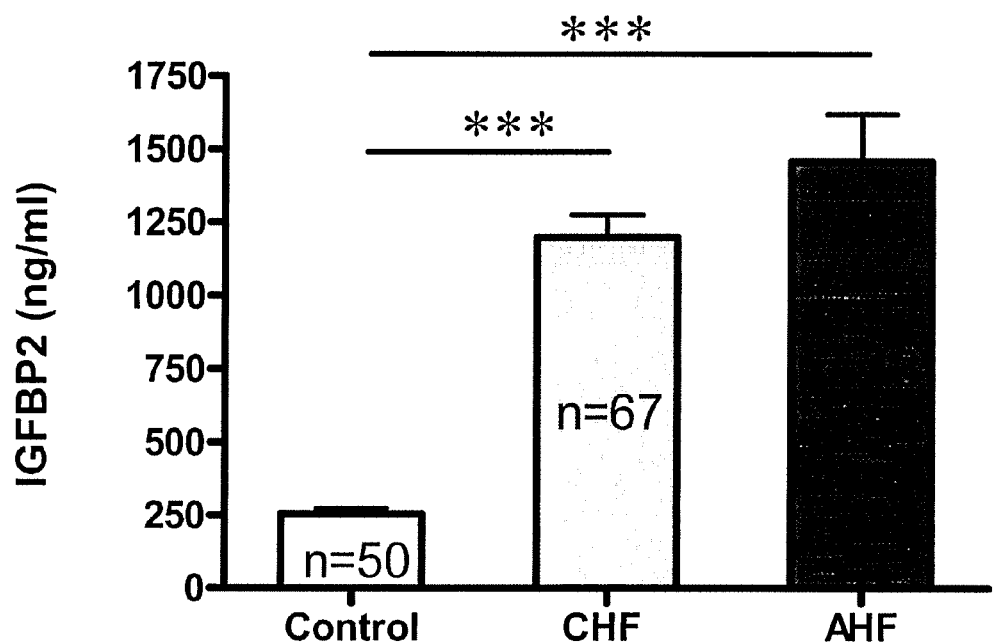

FIG. 2: Plasma concentration of IGFBP2 (ng/ml) in Control; Chronic Heart failure (CHF), and Acute heart failure (AHF) patients. Multiple comparison was performed with Anova and Bonferroni post hoc test (*** p<0.001).

Figure 3:
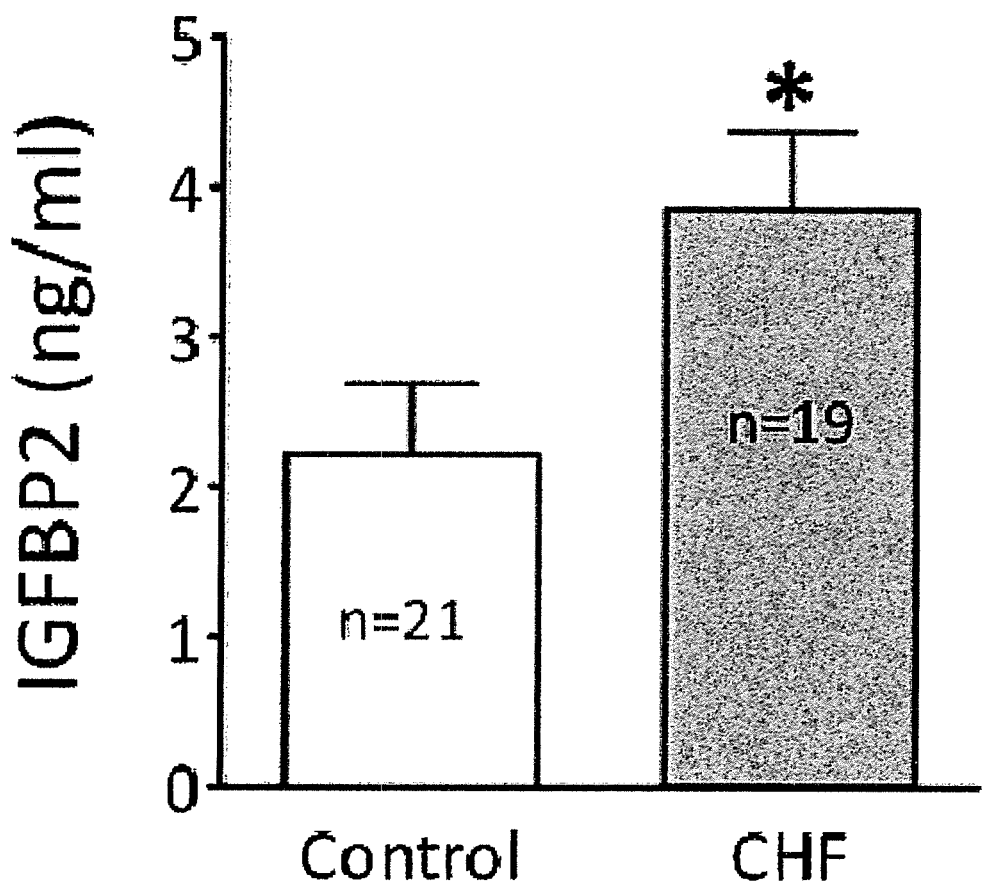

FIG. 3: Urine concentration of IGFBP2 (ng/ml). Control, n=21; Chronic Heart failure (CHF), n=19. Comparisons were performed using the Student t test where * is for p<0.001.

Figure 4:
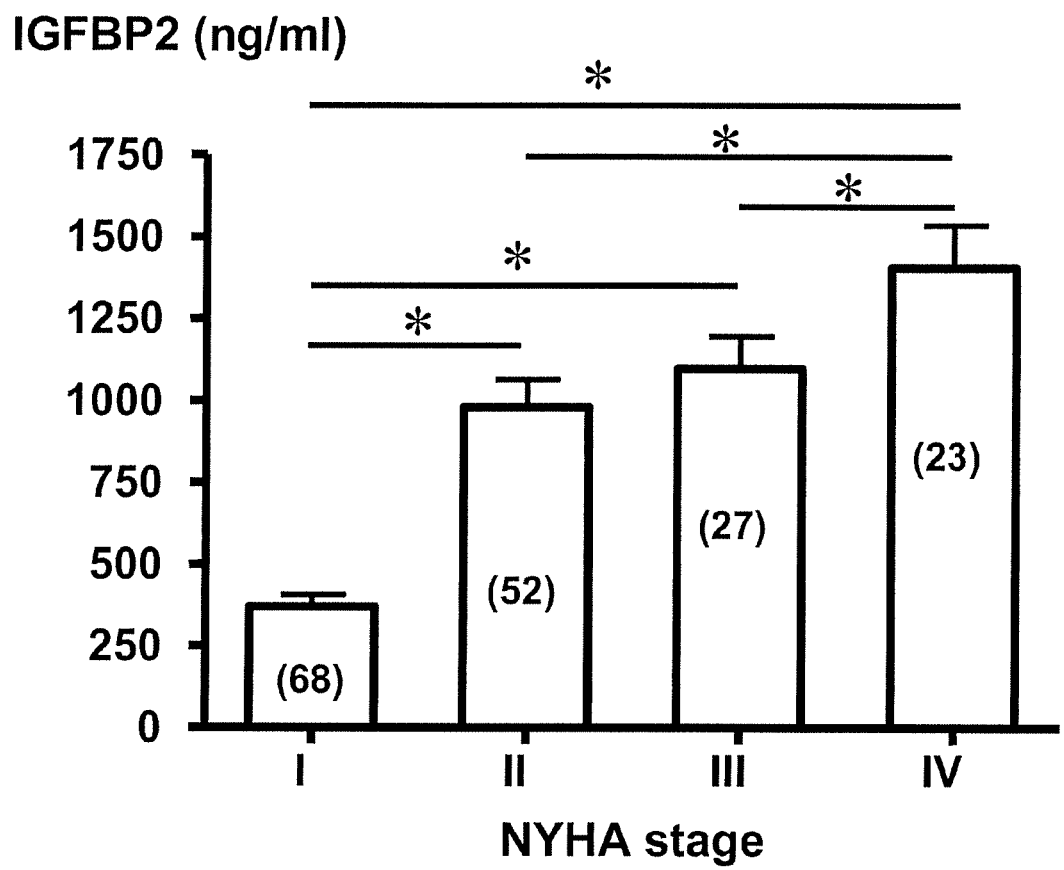

FIG. 4: Plasma concentration of IGFBP2 according to the NYHA classification of heart failure stage. Multiple comparison was performed with Anova and Bonferroni post hoc test (* p<0.01).

Figure 5:
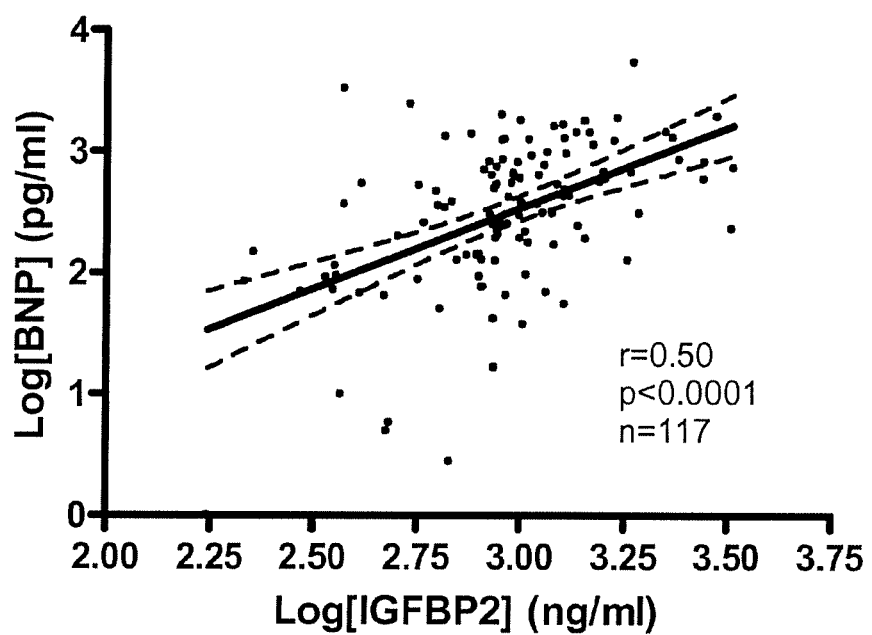

FIG. 5: Scatter plot of IGFBP2 versus BNP concentration in plasma. Estimated regression line is plotted including its 95% Confident interval (dashed lines).

Figure 6:
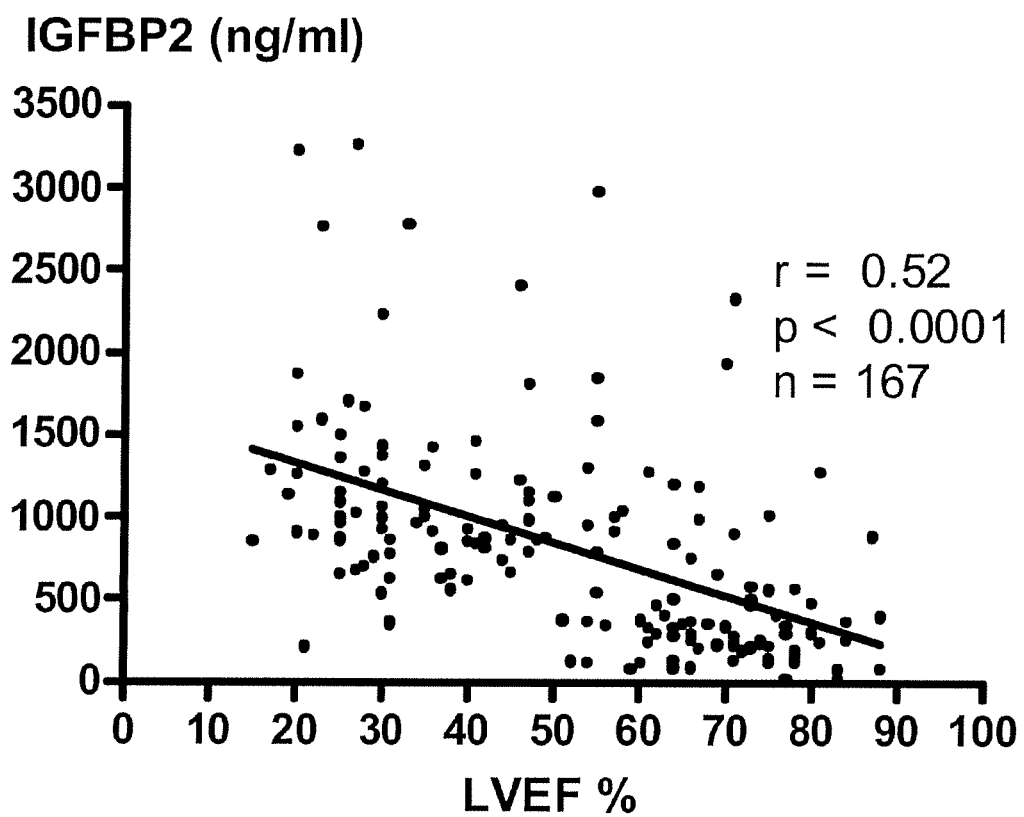

FIG. 6: Plasma concentration of IGFBP2 and the left ventricular ejection fractions are correlated. IGFBP2 Plasma concentration was measured by ELISA and left ventricular ejection fraction (LVEF) by transthoracic echocardiography.

Figure 7:
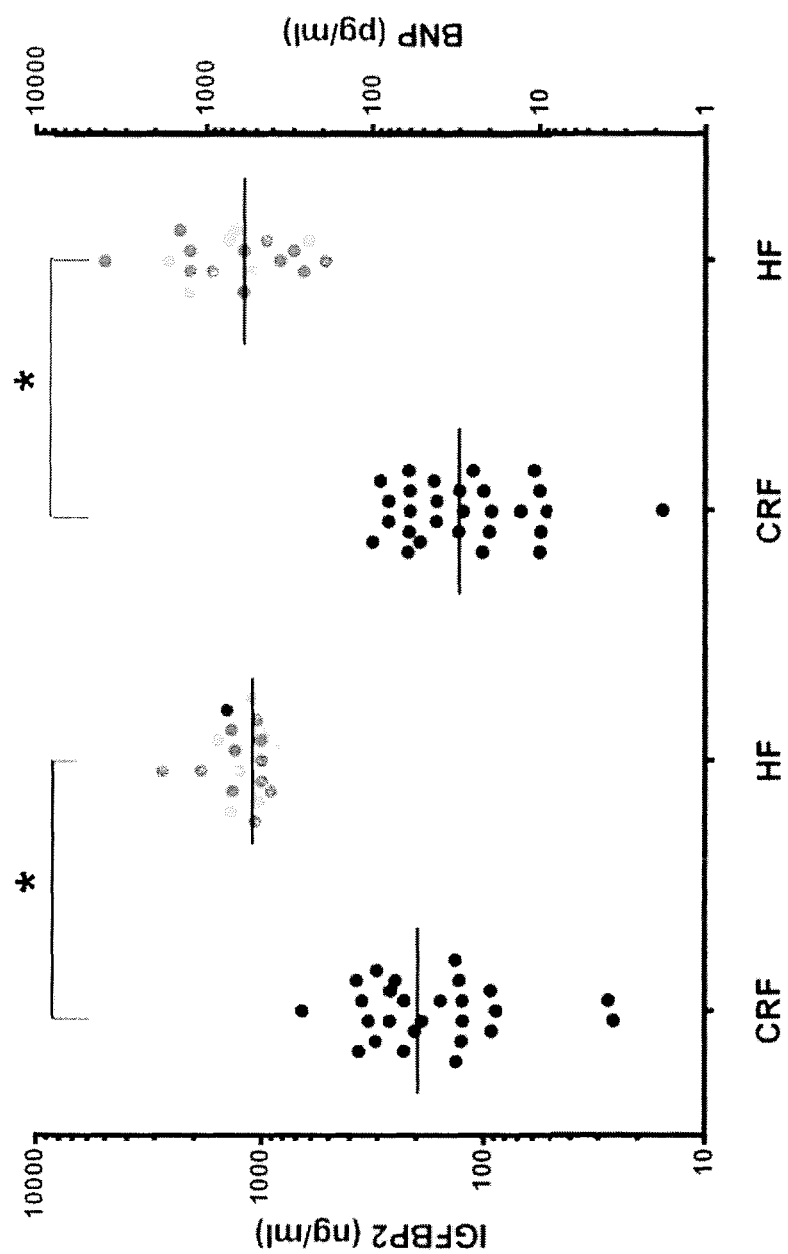

FIG. 7: IGFBP2 and BNP levels in plasma from the discovery-test set. Biomarkers measurements were performed with plasma from control patient with cardiovascular risk factors (CRF) or heart failure (HF) patients (acute and chronic, see FIG. 1). * Significant difference; p<0.05.

Figure 8:
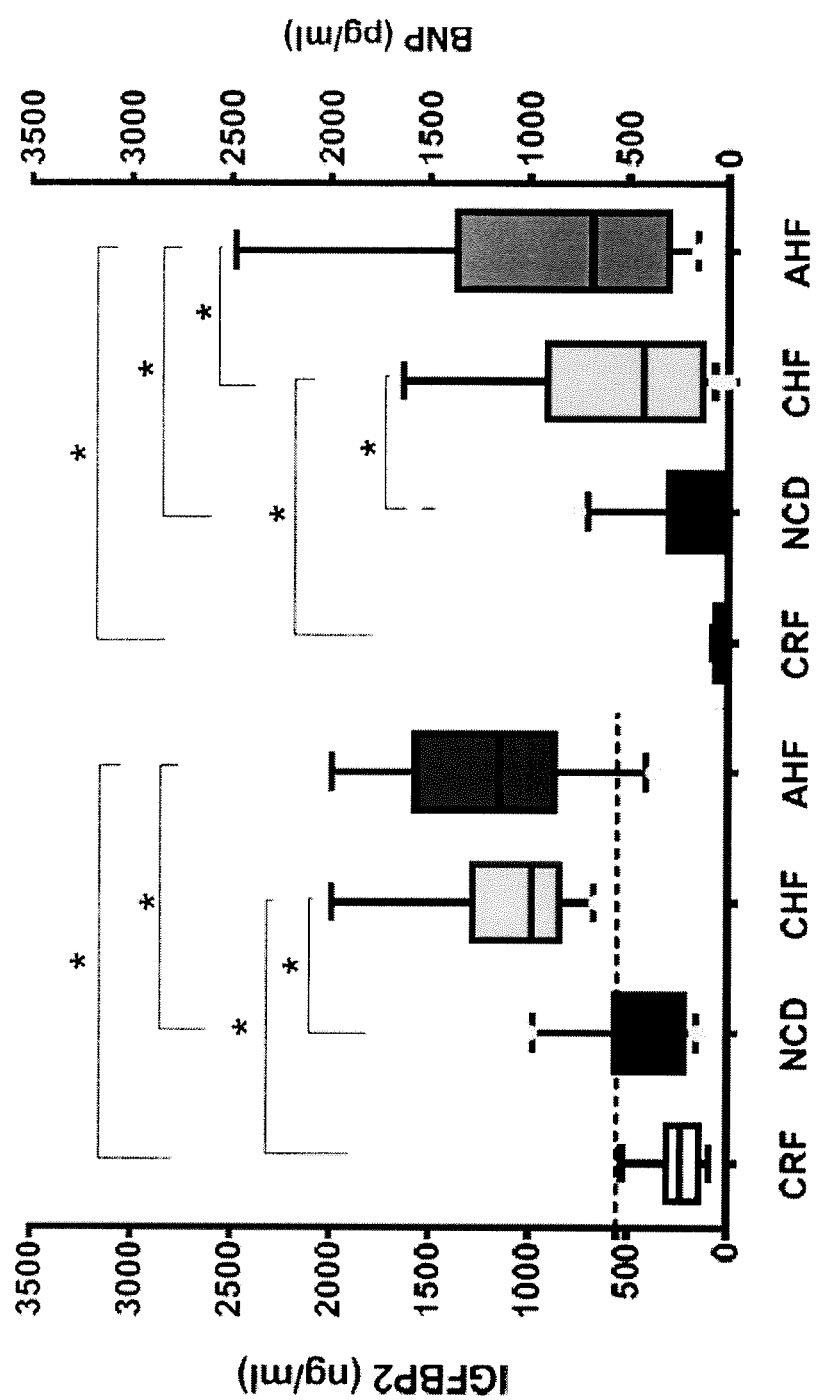

FIG. 8: IGFBP2 and BNP levels in plasma from the validation set.

(A) IGFBP2 and BNP levels were assessed in cardiovascular risk factor patients (CRF), non cardiac dyspnea (NCD), chronic heart failure (CHF) and acute heart failure (AHF) patients. * Significant difference; p<0.05. Horizontal dashed line corresponds to optimal cut-point at 556 ng/ml.

Figure 9:
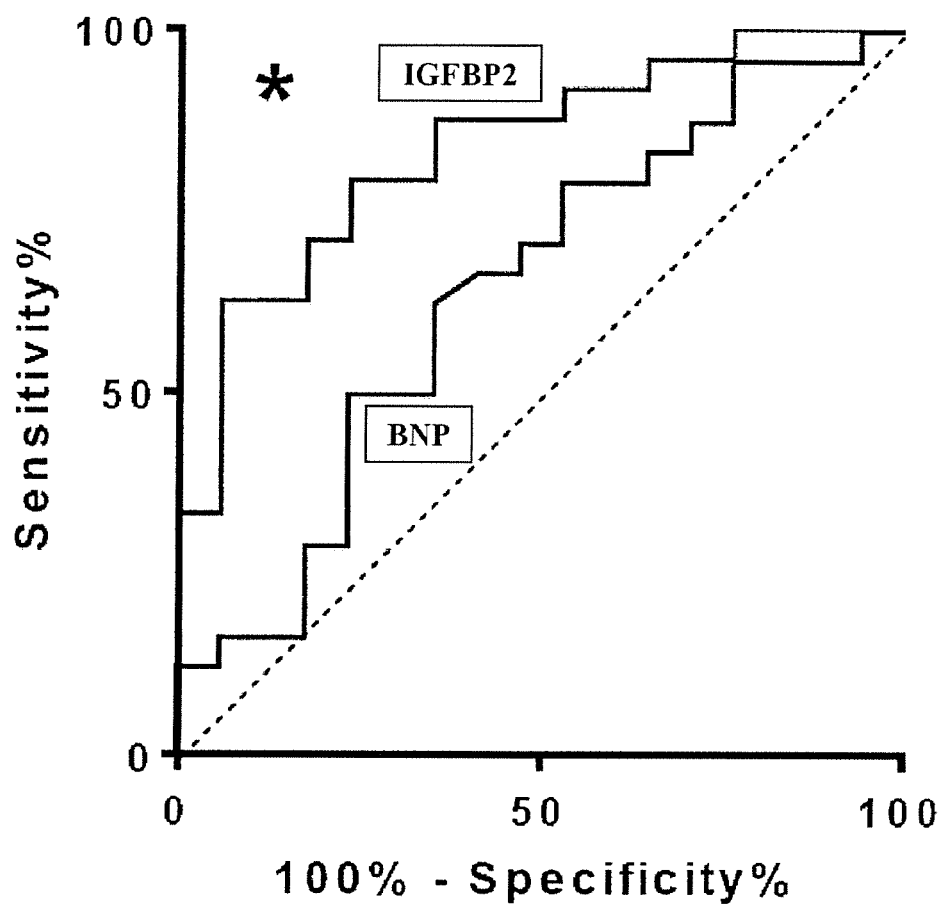

FIG. 9: IGFBP2 and BNP levels in plasma from NCD and AHF patients from the validation set.

ROC curve analysis for NCD (n=17) vs AHF (n=24) patients with a BNP comprise between 100 and 600 pg/ml. AUCs were 0.838 (CI 95%: 0.690-0.934) for IGFBP2 significantly different from AUC=0.5 p<0.0001 and 0.653 (CI 95%: 0.895-0.969) not significantly different from AUC=0.5 p=0.109 fot BNP. *Pairwise comparison of ROC curve were significant between BNP and IGFBP2 with p=0.034.

FIGS. 10A and 10B: Analysis of a rat model for ischemic heart failure.

(A) Echocardiography analysis. (B) qPCR analysis of IGFBP2 mRNA levels in rats hearts and livers. N=5 per group. * p<0.05. Rats had surgery at day 14 and tissues for mRNA analysis were collected at day 70.

TABLE 1

The discovery test-set demographic and clinical characteristics. This set was constituted of 28 cardiovascular risk factors patients (CRF) as "controls" that were compared to 12 acute heart failure (AHF) and 9 chronic heart failure (CHF) patients as "cases". LVEF: left ventricular ejection fraction.

|  | CRF (n = 28) | HF (n = 21) | P |
|---|---|---|---|
| Age, years | 53 ± 12 | 70 ± 15 | <0.001 |
| Sex, Female, % (F/M) | 36 (10/18) | 52 (11/10) | 0.262 |
| BMI | 28.0 ± 4.6 | 25.2 ± 5.8 | 0.076 |
| Cardiovascular risk factors |  |  |  |
| Hypertensive, % (n) | 50 (14) | 52 (11) | 1.000 |
| Diabete T2, % (n) | 14 (5) | 38 (8) | 0.190 |
| Dyslipedemia, % (n) | 79 (22) | 62 (13) | 0.222 |
| Obesity, % (n) | 28 (8) | 24 (5) | 0.528 |
| Smoking, % (n) | 14 (1) | 19 (4) | 0.150 |
| Cardiovascular history |  |  |  |
| Coronaropathy artery disease, % (n) | 0 (0) | 43 (9) | <0.001 |
| Hypertensive HCM, % (n) | 0 (0) | 14 (3) | 0.072 |
| Hereditary HCM, % (n) | 0 (0) | 5 (1) | 0.428 |
| Valvular heart disease, % (n) | 0 (0) | 9 (2) | 0.178 |
| Dilated cardiomyopathy, % (n) | 0 (0) | 20 (4) | 0.028 |
| Toxic cardiomyopathy, % (n) | 0 (0) | 20 (4) | 0.028 |
| Medication |  |  |  |
| ACE inhibitor, % (n) | 4 (1) | 38 (8) | 0.003 |
| ARAII, % (n) | 14 (4) | 20 (4) | 0.710 |
| Beta-blocker, % (n) | 7 (2) | 52 (11) | <0.001 |
| Diuretic, % (n) | 4 (1) | 90 (19) | <0.001 |
| Vitamin K antagonist, % (n) | 0 (0) | 28 (6) | 0.003 |
| Antiplatelet agent, % (n) | 10 (3) | 67 (14) | <0.001 |
| Statine, % (n) | 32 (9) | 52 (11) | 0.147 |
| Admission labs |  |  |  |
| BNP, pmol/ml | 30 [21-57] | 595 [333-1063] | <0.001 |
| Creatinine clairance, ml/min | 102 [87-122] | 56 [45-60] | <0.001 |
| C reactive protein, mg/l | 1.9 [1.4-2.3] | 31.0 [12.9-63.3] | <0.001 |
| Na+, mM | 140 ± 1 | 135 ± 6 | <0.001 |
| ALT, U/ml | 30 [26-40] | 40 [23-66] | 0.281 |
| Admission vitals |  |  |  |
| Mean Blood Pressure, mmHg | 101 ± 11 | 83 ± 20 | <0.001 |
| Heart rate, Bpm | 70 [68-75] | 85 [81-104] | <0.001 |
| Echocardiography |  |  |  |
| LVEF, % | 70 ± 9 | 31 ± 12 | <0.001 |
| LVEF <40%, % (n) | 0 (0) | 81 (17) | <0.001 |

TABLE 2

Differentially represented polypeptides determined by CE-MS. Areas under curve (AUC) are indicated for the 9 polypeptides that are better predictors for HF. "p" values unadjusted and after Bonferroni or Benjamini Hochberg (BH) adjustment.

| Polypeptide | unadj.wilcox-p-value | Adj. Bonferroni | Adj. BH | AUC |
|---|---|---|---|---|
| x64054 | 6.40e−09 | 1.39e−05 | 1.39e−05 | 0.988 |
| x53078 | 6.05e−08 | 1.32e−04 | 4.39e−05 | 0.947 |
| x102021 | 1.19e−07 | 2.58e−04 | 5.17e−05 | 0.945 |
| x69979 | 2.62e−07 | 5.69e−04 | 6.44e−05 | 0.934 |
| x52446 | 3.35e−07 | 7.28e−04 | 6.44e−05 | 0.929 |
| x13188 | 1.54e−08 | 3.35e−05 | 1.67e−05 | 0.929 |
| x3806 | 4.15e−07 | 9.02e−04 | 6.44e−05 | 0.925 |
| x140665 | 3.62e−07 | 7.86e−04 | 6.44e−05 | 0.925 |
| x91463 | 1.15e−07 | 2.49e−04 | 5.17e−05 | 0.923 |

TABLE 3

Validation set demographic and clinical characteristics, cardiovascular risk factors (CRF); non cardiac dyspnea (NCD), chronic heart failure (CHF) and acute heart failure (AHF) patients were recruited. LVEF: left ventricular ejection fraction.

|  | CRF (n = 39) | NCD (n = 43) | P | CHF (n = 58) | P | AHF (n = 39) | P |
|---|---|---|---|---|---|---|---|
| Age, years | 57 ± 11 | 66 ± 16 | 0.022 | 62 ± 13 | 0.022 | 73 ± 15 | <0.001 |
| Sex, Female, % (F/M) | 41 (16/23) | 54 (23/20) | 0.364 | 32 (19/40) | 0.498 | 54 (21/18) | 0.364 |
| BMI | 26.8 ± 4.3 | 25.0 ± 6.0 | 0.181 | 25.6 ± 4.2 | 0.173 | 27.4 ± 4.3 | 0.688 |
| Cardiovascular risk factors | | | | | | | |
| Hypertensive, % (n) | 31 (12) | 49 (21) | 0.150 | 38 (22) | 0.612 | 81 (31) | <0.001 |
| Diabete T2, % (n) | 15 (6) | 21 (9) | 0.717 | 30 (17) | 0.181 | 24 (9) | 0.567 |
| Dyslipedemia, % (n) | 80 (32) | 33 (14) | <0.001 | 59 (34) | 0.027 | 55 (21) | 0.015 |
| Obesity, % (n) | 31 (12) | 14 (6) | 0.116 | 14 (8) | 0.077 | 20 (8) | 0.437 |
| Smoking, % (n) | 10 (4) | 30 (13) | 0.050 | 14 (8) | 0.838 | 10 (4) | 0.709 |
| Cardiovascular history | | | | | | | |
| Coronaropathy artery disease, % (n) | 5 (2) | 14 (6) | 0.331 | 51 (30) | <0.001 | 52 (20) | <0.001 |
| Hypertensive HCM, % (n) | 0 (0) | 9 (4) | 0.150 | 8 (5) | 0.157 | 13 (5) | 0.044 |
| Hereditary HCM, % (n) | 0 (0) | 0 (0) | 0.740 | 8 (5) | 0.157 | 0 (0) | 0.740 |
| Valvular heart disease, % (n) | 0 (0) | 9 (4) | 0.150 | 20 (12) | 0.007 | 16 (6) | 0.033 |
| Dilated cardiomyopathy, % (n) | 0 (0) | 0 (0) | 0.740 | 24 (14) | <0.001 | 8 (3) | 0.239 |
| Toxic cardiomyopathy, % (n) | 0 (0) | 0 (0) | 0.740 | 8 (5) | 0.157 | 8 (3) | 0.239 |
| Medication | | | | | | | |
| ACE inhibitor, % (n) | 10 (4) | 21 (9) | 0.308 | 64 (37) | <0.001 | 37 (14) | 0.016 |
| ARAII, % (n) | 13 (5) | 19 (8) | 0.679 | 10 (6) | 0.960 | 21 (8) | 0.543 |
| Beta-blocker, % (n) | 18 (7) | 23 (10) | 0.749 | 73 (42) | <0.001 | 55 (21) | 0.002 |
| Diuretic, % (n) | 10 (4) | 56 (24) | <0.001 | 74 (43) | <0.001 | 89 (35) | <0.001 |
| Vitamin K antagonist, % (n) | 0 (0) | 30 (13) | <0.001 | 46 (27) | <0.001 | 29 (11) | 0.001 |
| Antiplatelet agent, % (n) | 10 (4) | 23 (10) | 0.205 | 55 (32) | <0.001 | 60 (23) | <0.001 |
| Statine, % (n) | 38 (15) | 21 (9) | 0.134 | 60 (35) | 0.056 | 37 (14) | 1.000 |
| Admission labs | | | | | | | |
| BNP, pmol/ml | 25 [21-48] | 95 [61-169] | <0.001 | 423 [303-636] | <0.001 | 686 [370-1207] | <0.001 |
| Creatinine clairance, ml/min | 86 [83-96] | 73 [58-87] | 0.013 | 58 [51-72] | <0.001 | 42 [31-53] | <0.001 |
| C reactive protein, mg/l | 1.9 [1.2-2.7] | 9.6 [4.6-23.5] (39) | <0.001 | 8.6 [6.3-13.0] | <0.001 | 26.0 [19.7-47.3] | <0.001 |
| Na+, mM | 140 ± 2 | 138 ± 4.3 | 0.005 | 138 ± 3 | <0.001 | 137 ± 6 | <0.001 |
| ALT, U/ml | 31 [26-38] | 23 [19-28] | 0.006 | 30 [25-38] | 0.982 | 38 [24-51] | 0.471 |

TABLE 3-continued

Validation set demographic and clinical characteristics, cardiovascular risk factors (CRF); non cardiac dyspnea (NCD), chronic heart failure (CHF) and acute heart failure (AHF) patients were recruited. LVEF: left ventricular ejection fraction.

| | CRF (n = 39) | NCD (n = 43) | P | CHF (n = 58) | P | AHF (n = 39) | P |
|---|---|---|---|---|---|---|---|
| Admission vitals | | | | | | | |
| Mean Blood Pressure, mmHg | 98 ± 11 | 94 ± 14 | 0.120 | 85 ± 12 | <0.001 | 89 ± 24 | 0.037 |
| Heart rate, Bpm | 65 [60-67] | 88 [81-95] | 0.006 | 76 [70-84] | <0.001 | 91 [84-99] | <0.001 |
| Echocardiography | | | | | | | |
| LVEF, % | 70 ± 10 | 64 ± 12 | 0.010 | 36 ± 13 | <0.001 | 42 ± 19 | <0.001 |
| LVEF <40%, % (n) | 0 (0) | 0 (0) | 0.740 | 60 (35) | <0.001 | 50 (23) | <0.001 |

TABLE 4

Correlations of IGFBP2 and BNP levels with clinical characteristics. Rho: Spearman rank correlation coefficient, n = 228. Rho >0.5 moderate to high relationship are in bold.

| | IGFBP2 | | | BNP | | |
|---|---|---|---|---|---|---|
| | rho | p | n | rho | p | n |
| Age, years (n) | 0.397 | <0.0001 | 179 | 0.331 | <0.0001 | 177 |
| Sex, Female, % (F/M) | 0.006 | 0.9358 | 180 | 0.053 | 0.4832 | 178 |
| BMI (n) | −0.288 | 0.0002 | 166 | −0.209 | 0.0071 | 165 |
| Cardiovascular risk factors | | | | | | |
| Hypertensive, % (n) | 0.130 | 0.0839 | 179 | 0.081 | 0.2834 | 178 |
| Diabete, % (n) | 0.180 | 0.0161 | 179 | 0.090 | 0.2335 | 178 |
| Dyslipedemia, % (n) | −0.228 | 0.0021 | 179 | −0.250 | 0.0007 | 178 |
| Obesity, % (n) | −0.243 | 0.0010 | 180 | −0.158 | 0.0357 | 178 |
| Smoking, % (n) | 0.011 | 0.8834 | 180 | 0.047 | 0.5370 | 178 |
| Cardiovascular history | | | | | | |
| Coronaropathy artery disease, % (n) | 0.381 | <0.0001 | 179 | 0.371 | <0.0001 | 178 |
| Hypertensive HCM, % (n) | 0.156 | 0.0368 | 179 | 0.067 | 0.3740 | 178 |
| Hereditary HCM, % (n) | 0.141 | 0.0595 | 179 | 0.204 | 0.0063 | 178 |
| Valvular heart disease, % (n) | 0.302 | <0.0001 | 179 | 0.281 | 0.0001 | 178 |
| Dilated cardiomyopathy, % (n) | 0.182 | 0.0147 | 179 | 0.211 | 0.0046 | 178 |
| Toxic cardiomyopathy, % (n) | 0.205 | 0.0060 | 179 | 0.184 | 0.0140 | 178 |
| Medication | | | | | | |
| ACE inhibitor, % (n) | 0.256 | 0.0005 | 179 | 0.245 | 0.0010 | 178 |
| ARAII, % (n) | −0.044 | 0.5616 | 179 | −0.022 | 0.7736 | 178 |
| Beta-blocker, % (n) | 0.325 | <0.0001 | 179 | 0.364 | <0.0001 | 178 |
| Diuretic, % (n) | 0.704 | <0.0001 | 179 | 0.674 | <0.0001 | 178 |
| Vitamin K antagonist, % (n) | 0.268 | 0.0003 | 179 | 0.311 | <0.0001 | 178 |
| Antiplatelet agent, % (n) | 0.380 | <0.0001 | 179 | 0.311 | <0.0001 | 178 |
| Statine, % (n) | 0.074 | 0.3232 | 179 | 0.061 | 0.4155 | 178 |
| Admission labs | | | | | | |
| BNP, pmol/ml (n) | 0.773 | <0.0001 | 178 | — | — | — |
| Creatinine clairance μmol/l (n) | −0.681 | <0.0001 | 178 | −0.587 | <0.0001 | 177 |
| C reactive protein, mg/l (n) | 0.615 | <0.0001 | 179 | 0.614 | <0.0001 | 177 |
| Na+, mM (N) | −0.331 | <0.0001 | 179 | −0.409 | <0.0001 | 178 |
| ALT, U/ml (N) | 0.075 | 0.3245 | 174 | 0.115 | 0.1316 | 173 |
| Mean Blood Pressure, mmHg (n) | | | | | | |
| Heart rate, Bpm (n) | −0.419 | <0.0001 | 169 | −0.397 | <0.0001 | 168 |
| Echocardiography | 0.410 | <0.0001 | 172 | 0.452 | <0.0001 | 171 |
| LVEF, % (n) | <0.653 | <0.0001 | 178 | −0.669 | <0.0001 | 176 |

TABLE 5

External validation cohort demographic and clinical characteristics. LVEF: left ventricular ejection fraction.

| | COPD (n = 10) | AHF (n = 30) | P |
|---|---|---|---|
| Age, years | 57 ± 10 | 73 ± 10 | <0.001 |
| Gender, Female, % (F/M) | 30 (3/7) | 23 (7/23) | 0.689 |
| Cardiovascular risk factors | | | |
| Hypertensive, % (n) | 30 (3) | 63 (19) | 0.140 |
| Diabete T2, % (n) | 40 (4) | 43 (13) | 1.000 |
| Dyslipedemia, % (n) | 30 (3) | 47 (14) | 0.470 |
| Obesity, % (n) | 10 (1) | 6 (2) | 1.000 |
| Cardiovascular history | | | |
| Coronaropathy artery disease, % (n) | 10 (1) | 43 (13) | 0.069 |
| Valvular heart disease, % (n) | 0 (0) | 30 (9) | 0.080 |
| Clinical presentation | | | |
| Acute heart failure | — | 30 (9) | — |
| Acutely decompensated heart failure, % (n) | — | 60 (18) | — |
| Pulmonary edema, % (n) | — | 10 (3) | — |

TABLE 5-continued

External validation cohort demographic and clinical characteristics.
LVEF: left ventricular ejection fraction.

|  | COPD (n = 10) | AHF (n = 30) | P |
|---|---|---|---|
| Medication |  |  |  |
| ACE inhibitor or ARAII, % (n) | 30 (3) | 63 (19) | 0.140 |
| Beta-blocker, % (n) | 0 (0) | 57 (17) | 0.010 |
| Diuretic, % (n) | 40 (4) | 80 (24) | 0.041 |
| Vitamin K antagonist, % (n) | 10 (1) | 47 (14) | 0.059 |
| Antiplatelet agent, % (n) | 30 (3) | 60 (18) | 0.148 |
| Statine, % (n) | 20 (2) | 57 (17) | 0.691 |
| Admission labs |  |  |  |
| BNP, pmol/ml | 14 [10-19] | 1782 [1340-2773] | <0.001 |
| Creatinine, µmol/l | 80 [65-100] | 120 [98-142] | 0.015 |
| C reactive protein, mg/l | 4.0 [0.0-14.5] | 10 [0.7-19.5] | 0.209 |
| Na$^+$, mM | 139 ± 3 | 136 ± 7 | <0.043 |
| Admission vitals |  |  |  |
| Mean Blood Pressure, mmHg | 98 ± 13 | 93 ± 17 | 0.443 |
| Heart rate, Bpm | 104 ± 28 | 88 ± 26 | 0.107 |
| Echocardiography |  |  |  |
| LVEF, % | — | 35 [20-60] | — |

EXAMPLES

Example 1: First Patient's Analysis

Material & Methods
Patients:
1. Population:

We performed a monocentric transversal study with the inclusion of over 200 patients between November 2010 and March 2011 from the Toulouse Rangueil University Hospital. Three groups of patients were constituted: Chronic heart failure, (CHF), Acute heart failure (AHF) and control. All patients have signed a consent agreement and the biosample collection was approved by the French ministry of health, CCTIR, CNIL and ethic committee (CPP). Patients under 18 years old or not able to understand or to sign the agreement were excluded as well as kidney failure or transplanted patients.

a. Chronic heart failure patients (CHF):

We included patients with a known stable CHF (>3 months without any decompensation) ranging from NYHA stage I to IV with miscellaneous etiologies (ischemic cardiopathy (CMI), valvular (CMV), post-hypertensive (CMH post-HTA), hypertrophic genetic cardiomyopathy (CMH gene), primary dilated cardiomyopathy or toxic (CMD)), Right ventricle arythmogenic dysplasia arythmogen and congenital cardiomyopathy. Inclusion required a clear diagnosis of heart failure (clinical, history of the disease, transthoracic echocardiography (TTE) and/or BNP). These patients were admitted in several cardiology services (hospitalization, consultation form Pr Galinier and Pr Carrie units) after their admission for heart failure.

b. Acute Heart Failure (AHF):

We included patients admitted for acute cardiac decompensation whatever the type was (left, right, mixed, low output, cardiogenic choc) to be able to identify putative CHF and AHF biomarkers.

c. Control:

Control patients were included through the artherosclerosis prevention department of Rangueil University Hospital during day hospitalization.

2. Clinical Data:

For all patients, anthropometric data (weight, height, gender) clinical history, electrocardiographic and biological data (plasmatic sodium, creatinine, hepatic status, prothrombine, CRP, hematocrite and hemoglobin) were collected. BNP levels data were collected for CHF and AHF patients. All these examinations were requested during the treatment of the by the physician in charge of the patients and were performed to monitor the heart failure stage but also the kidney and liver function, hydratation and inflammatory level. All medications were recorded.

3. Echocardiography:

Transthoracic echocardiography (TTE) was performed for all subjects included by a single cardiologist on a dedicated machine (Kontron) allowing for data collection during procedure and post-processing of the data using the software My Lab Desk—Kontron for each patient.

TTE allowed for systematic volumes and diameters measurements, left ventricle systolic and diastolic function. In addition, right ventricle function was analyzed as well as aortic, mitral or tricuspid valvulopathies. TTE was considered as «gold standard» for heart failure diagnosis that was completed with its etiology according to the European and American current recommendations.

Biological Samples:

Urine were collected in standard polypropylene tubes and immediately frozen and maintained at −80° C. Plasma were collected on EDTA tubes, centrifuged, aliquoted on ice and immediately frozen at −80° C.

Analytical Methods:

CE-MS was performed using standard procedure [Mischak, H. et al., 2010]. Briefly, peptides were electrophoretically separated on 90 cm long and 50 µm diameter silice capilar (Beckmann-Coulter, Fullerton, Calif., USA) coupled to a ESI-TOF mass spectrometer (electrospray ionisation—time of flight) (MicroTOF, Brucker-Daltonic, Bremen, Germany). CE-MS buffer was 20% (v/v) acetonitrile and 250 mM formic acid in HPLC water. Electrophoretic separation is performed during 60 mM under an electric field (+35 to −40 kV) leading to a 13 µA intensity. Capillary temperature is maintained to +35° C. during runs.

Enzyme-linked immunosorbent assay (ELISA) IGFBP2 quantization was performed using R&D SYSTEMS EUROPE LTD reagents according to the manufacturer ELISA reagent protocol.

Results

We first screened the urinary proteome of 50 patients (9 CHF, 13 AHF, 28 healthy controls apparied for age sex and risk factor), which led to reveal a panel of polypeptides specific to HF. One polypeptide (x64054, mass 1878,792 Da; Capillary electrophoresis time t=20.72 min) seemed very relevant because it could discriminate AHF and CHF with a high specificity and sensibility based on CE-MS data (AUC=0.99; p<0.0001). Using MALDI-TOF analysis, we identified this putative biomarker as a fragment of the Insulin-like growth factor-binding protein 2 (IGFBP2).

The validation of IGFBP2 as a putative biomarker was performed by ELISA using both plasma and urine concentration measurements in 200 patients. ROC curve analysis provided an AUC value of 0.988, p<0.0001 (FIG. 1). Clearly plasma (FIG. 2) and urinary (FIG. 3) concentration of IGFBP2 are strongly enhanced in CHF and AHF patients. Moreover the elevation of IGFBP2 concentration in plasma was dependant on the severity of heart failure as indicated by the NYHA classification (FIG. 4). Furthermore, we noticed that IGFBP2 and BNP levels were weakly correlated giving more importance to this new biomarker as an almost independent indicator (FIG. 5). Finally, we observed that the IGFBP2 plasma level and the left ventricular ejection fraction were negatively correlated, indicating a physiological link between bloodstream IGFBP2 level and the heart function and bringing IGFBP2 levels as possible estimate of the heart pump status (FIG. 6). Therefore, we propose that elevated IGFBP2 concentration could be used as a biomarker of heart failure.

Example 2: Second Patient's Analysis

Material & Methods
Patient Inclusions

Two independent cohorts were used in this study. A discovery-validation cohort with 228 patients who were recruited between November 2010 and November 2011 at the Rangueil University Hospital (Toulouse, France) and an external validation cohort with 40 patients who were recruited between 2009 and 2011 at the Lariboisière University Hospital (Paris, France).

To focus on specific biomarkers of heart failure without prejudice to etiology or severity of the heart failure, the case group of the discovery-validation cohort was constituted of patients suffering from chronic (CHF) or acute (AHF) heart failure. CHF patients had a known stable HF with >3 months without any decompensation episodes, whatever the stage of clinical severity (stage I to IV of NYHA classification) and, regardless of etiology. Diagnosis of heart failure had been formally established from clinical observations, heart disease follow-up, transthoracic echocardiography (TTE) and BNP monitoring. These patients were included during their regular scheduled visit at the hospital. AHF patients were recruited whatever the clinical presentation (left, right, mixed, low flow-cardiogenic shock.

The control group of the discovery-validation cohort was constituted of patients without HF but with cardiovascular risk factors (CRF) or CRF and non cardiac dyspnea (NCD) for the discovery step and the validation step, respectively. CRF patients were recruited during their scheduled visit at the atherosclerosis prevention center of the Rangueil University Hospital. Inclusion in this group required the exclusion of all patients with a history, clinical signs, biological, or echocardiographic evidence of heart failure (systolic or diastolic dysfunction).

External validation cohort was constituted at the Lariboisière University Hospital (Paris, France) with COPD patients (with BNP<20 pg/ml to test "pure" COPD without any right or left cardiac stress) as control patient and AHF patients as cases patients.

For all subjects anthropometric data (weight, height, gender), clinical history, biological data and electrocardiographic were collected (Tables 1, 3, 5). All these examinations were performed during the treatment by the physician in charge of the patients and were performed to monitor the heart failure stage but also the kidney and liver function, hydratation and inflammatory level. All medications were recorded.

TTE was performed for all subjects included by a single cardiologist. Echocardiography (Konton Imagic, Kontron, Saint German en Laye, France) allowed for systematic volumes and diameter measurements, left ventricle systolic and diastolic function and ejection fraction measurements. Patients with renal dialysis or transplant (stage 5D and 5T) were excluded.

The research protocol was registered in a clinical database (ClinicalTrials.gov NCT01024049) conforms to the ethical guidelines of the 1975 Declaration of Helsinki. The protocol was approved by the institution's human research (COSSEC) and regional ethics committee (Comite de Protection des Personnes (CPP) #DC 2008-452). Written informed consent was obtained from all participants and/or their legally authorized representatives.

Discovery and Validation Sets

We first randomly constituted a discovery-test set of 49 subjects out of the 228 patients from discovery-validation cohort. Twenty-one HF patients with 9 out of the 67 AHF and 12 out of the 51 AHF constituted the cases subset and 28 out the 67 CRF patients constituted the controls subset. Urines from these 49 subjects were used for CE-MS proteomic analysis (Table 1). X64054 peptide isolated through this analysis was further identified below as IGFBP2 and tested in plasma of the discovery-test set. Furthermore two validation cohorts were constituted. The first comprising patients from Toulouse university hospital (Table 3); The validation set included 179 patients with a control subset constituted of 39 CRF and 43 NCD and a case subset constituted of 39 AHF and 58 CHF.

A second validation cohort was constituted with 40 patients from Paris Lariboisière University Hospital. This external validation cohort included 10 COPD and AHF patients (Table 5).

Biological Samples

All subjects were venesected and peripheral venous blood was drawn into sodium/EDTA tubes. After centrifugation at 1500 g at 4° C. for 10 min, plasma was separated, aliquoted and stored at −80° C. until assayed. Subjects also provided a morning urine sample, and 20 ml was collected into polypropylene collection pot, aliquoted and stored as above.

Analytical Methods

Sample Preparation and Capillary Electrophoresis Coupled to Mass Spectrometry (CE-MS) Analysis All participants collected morning urine samples the day of the echocardiographic examinations.

Aliquots were stored at −80° C. until the time of processing. Urine samples were then processed as previously described 13 and then resuspended in HPLC-grade water shortly before CE-MS analyses. CE-MS analysis was performed as described using a P/ACE MDQ capillary electrophoresis system (Beckman Coulter, Villepinte, France) on-line coupled to a MicroQTOF MS (Bruker Daltonics, Bremen, Germany). The ESI sprayer (Agilent Technologies, Palo Alto, Calif., USA) was grounded, and the ion spray interface potential was set between −4.0 and −4.5 kV. Data acquisition and MS acquisition methods were automatically controlled by the CE via contact-close-relays. Spectra were accumulated every 3 s, over a range of m/z 350 to 3000. Details on accuracy, precision, selectivity, sensitivity, reproducibility, and stability of the CE-MS method have been provided previously.

Data Processing

Mass spectra were processed using MosaiquesVisu software (Mosaiques, Hannover, Germany), including peak picking, deconvolution, and de-isotoping. Migration time and peak intensity were normalized using internal polypeptide standards. These fragments are believed to be the result of normal biological processes and appear to be unaffected by any disease state studied to date on the basis of 20,000 samples in our database. The resulting peak list characterizes each polypeptide by its molecular mass, normalized capillary electrophoresis migration time, and normalized signal intensity. All detected polypeptides were deposited, matched, and annotated in a Microsoft SQL database, allowing further analysis and comparison of multiple patient groups.

Statistical Methods and Identification of Biomarkers

We compared means and proportions of clinical and echocardiographic characteristics of the discovery and test samples by means of a t-test and the x2 statistics, respectively, using SAS software, version 9.1.3 (SAS Institute, Cary, N.C., USA). In the discovery phase, we compared the natural logarithm-transformed signal amplitude of the CE-MS urinary polypeptide profile between patients and controls using the Wilcoxon rank sum test. This non-parametric test is suitable for skewed proteomic data. We tested the null hypothesis that patients and controls have the same continuous distribution of signal amplitude of the CE-MS urinary polypeptide profile. The signal amplitude represents the calibrated counts (intensity) recorded by the mass spectrometry device. Statistical adjustment for multiple testing was performed by applying Benjamini-Hochberg correction. We searched for a cluster of urinary polypeptides discriminating between cases and controls based on the distribution of biomarkers in individual subjects. For each case and each control, the selected polypeptides were combined into a single summary variable, using the support-vector machine-based MosaCluster software, version 1.6.5. In the test set, researchers blinded to the clinical condition of the study participants measured the cluster polypeptides. After breaking the code, we calculated the sensitivity and the specificity based on tabulating the number of correctly classified samples in the test set, using receiver operating characteristic (ROC) plots. The area under the ROC curve (AUC) provides a single measure of overall accuracy that is independent of any particular threshold.

Sequencing

The urine samples were analysed on a Dionex Ultimate 3000 RSLS nano flow system (Dionex, Camberly UK), essentially as described (Carty et al., 2011; Metzger et al., 2012). The samples (5 µl) were loaded onto a Dionex 100 µm×2 cm 5 µm C18 nano trap column at a flowrate of 5 µl/min by a Ultimate 3000 RS autosampler (Dionex, Camberley UK) The composition of the loading solution was 0.1% formic acid and acetonitrile (98:2). Once loaded onto the trap column the sample was then washed off into an Acclaim PepMap C18 nano column 75 µm×15 cm, 2 µm 100 Å at a flowrate of 0.3 µm/min. Elution was performed with a linear gradient of solvent A, 0.1% formic acid and acetonitrile (98:2) against solvent B, 0.1% formic acid and acetonitrile (20:80) starting at 1% B for 5 minutes rising to 30% at 90 minutes then to 50% B at 120 minutes. The trap and nano flow column were maintained at 35° C. in a column oven in the Ultimate 3000 RSLC. The eluent from the column was directed to a Proxeon nano spray ESI source (Thermo Fisher Hemel UK) operating in positive ion mode then into an Orbitrap Velos FTMS. The ionisation voltage was 2.5 kV and the capillary temperature was 200° C. The mass spectrometer was operated in MS/MS mode scanning from 380 to 2000 amu. The fragmentation method was HCD at 35% collision energy. The ions were selected for MS2 using a data dependant method with a repeat count of 1 and repeat and exclusion time of 15 s. Precursor ions with a charge state of 1 were rejected. The resolution of ions in MS1 was 60,000 and 7,500 for HCD MS2. Data files from experiments performed on the HCD-enabled LTQ were searched against the IPI human non-redundant database using Thermo Proteome Discoverer, without any enzyme specificity. No fixed modification was selected, and oxidation of methionine and proline were set as variable modifications. Mass error window of 10 ppm and 0.05 Da were allowed for MS and MS/MS, respectively. For further validation of obtained peptide identifications, the strict correlation between peptide charge at the working pH of 2 and CE-migration time was utilized to minimize false-positive identification rates 17. Calculated CE-migration time of the sequence candidate based on its peptide sequence (number of basic amino acids) was compared to the experimental migration time. CE-migration time deviations below ±2 min corresponding to the CE-MS measurement were accepted.

Immune Methods

Western blot were performed as already published 18 using rabbit monoclonal anti-human IGFBP2 antibody, clone EPR3380(2) (Cliniscences, Nanterre, France). IGFBP2 enzyme-linked immunosorbent assay (R&D Systems, Inc., Minneapolis, Minn., USA) was used to measure human IGFBP2 as per the manufacturer's specifications.

mRNA Extractions, Reverse Transcription (RT) and Real-time Quantitative PCR (qPCR)

mRNA extractions and RT-qPCR was performed as already described using the different primers as already performed [Harmancey R et al, 2007].

Statistical Analysis

Because of the very large amount of signals in comparison to the number of patients tested in CE-MS analysis, only signal with a signal to noise ratio over 4 times the background were kept. Unless otherwise specified, continuous variables are presented as means (±SD) categorical variables as percentages. For continuous variables, a Student's t-test or Mann-Whitney rank sum test when normality test failed or for categorical variables a chi square test was used to determine their statistical differences between groups. Statistical analyses were performed using R computation language (http://www.R-project.org) and Medcalc (Medcalc, version 11.6.0.0, Medcalc software bva, Belgium).

Results

Discovery Study

Demographic and clinical data of the discovery-test set are presented in Table 1. Significant differences between control and HF patients for medication, admission labs, echocardiography and admission vitals parameters are in agreement with their clinical status Thus, plasma BNP and CRP concentrations were significantly higher in HF patients whereas creatinine clearance, sodium concentration were reduced. Moreover, mean blood pressure and ejection fraction (EF) were reduced in HF patients. HF patients also had an increased heart rate. HF patients and were older than the control subjects (70±15 vs 53±12; p<0.001). 43% of the HF patients had a history of CAD. Cardiovascular risk factors were similarly represented in the two groups.

Differentially Represented Polypeptides Determined by CE-MS and Identification of a New Putative HF Biomarker.

We aimed at detecting putative biomarkers profiles that could be a signature HF using CE-MS analysis of urine samples as a first step. Based on the urine proteome analysis of the AHF and CHF patients (all stages and etiologies) and CRF control subjects, we have defined a polypeptide set specific to HF (9 polypeptides with AUC≥0.923, p<0.001 (Benjamini Hochberg multiple testing correction) (Table 2). One polypeptide (x64054, mass 1878.792 Da; electrophoresis time t=20.72245) seemed very interesting because it showed an excellent discriminating power for HF with and AUC of 0.988, p=1.39.10-5. Therefore, we focused on this peptide and could successfully identify it as the insulin like growth factor binding protein 2 (IPI:IPI00297284.1). We first checked the presence of IGFBP2 in human urine and blood and observed that IGFBP2 was more abundant in plasma that in urine (data not shown). ELISA analysis of IGFBP2 urinary concentration revealed that the concentration was 505±198 (n=35) fold lower than in plasma (not shown). Because of this observation, we further analyzed IGFBP2 in plasma samples by ELISA.

IGFBP2 Plasma Concentration

Analysis of IGFBP2 in plasma showed a significant increase in heart failure patients vs control individuals with 1350±635 (p<0.001) and 214±136 ng/ml, respectively (FIG. 7). BNP levels in these patients displayed with a higher concentration in HF than in control patients; 806±693 and 39±28 (p<0.001), respectively (FIG. 7).

Validation Study

Demographic and clinical data of patients included in the validation set are presented in Table 3. CRF patients have cardiovascular risk factors without any symptoms or objective parameters of HF. AHF patients were the oldest group. AHF Patients had significant comorbid conditions, including hypertension (81%) coronary heart disease (52%) and diabetes mellitus (24%). Most patients were on diuretics (89%) and antiplatelet agents (60%). Age distribution of patients of the CHF group is nestled in the control group between CRF and NCD groups. The CHF patients were 62±13 years old with 68% male and the LVEF was ≤45% in 42 patients. Patients had significant comorbid conditions, including hypertension (37%) coronary heart disease (51%) and diabetes mellitus (30%). Again, most patients were on diuretics (78%) and antiplatelet agents (54%). There is no significant difference for gender between the groups. IGFBP2 concentrations were significantly increased in CHF and AHF vs CRF or NCD patients. This increase of IGFBP2 levels followed the similar pattern as BNP levels in this set of patients (FIG. 8). ROC curve analysis of CRF and NCD patients vs CHF and AHF patients showed an area under curve (AUC) of 0.933 for IGFBP2 with 0.81 Youden index associated with IGBP2>556 ng/ml which was higher than BNP (0.870; p=0.038). Logistic regression of IGFBP2+BNP raised the AUC to 0.942 but did not significantly increased the performance of IGFBP2 (data not shown).

IGFFBP2 was further tested for cardiac diagnostic of acute dyspnea patients. Values of IGFBP2 and BNP concentrations from these acute dyspnea patients are presented to displays the global distribution of the patients (data not shown). The ROC curve analysis of NCD vs AHF patients displayed an increased AUC for IGFBP2+BNP vs BNP (0.925 vs 0.859; p=0.04). In these groups of patients, IGFBP2 discrimination performance was not significantly different from the one of BNP (data not shown). A clear difference between BNP and IGFBP2 diagnostic performance was seen when the plasma BNP level was its poor diagnosis zone, which was extended here from 100 to 600 pg/ml which corresponded for its lower level to the rule-out concentration and 600 pg/ml which was defined as a reasonable higher cut-off value to rule-in HF. In contrast to BNP, which had no diagnostic value (AUC=0.643; 95% CI: 0.479-0.787) in this zone of concentrations, IGFBP2 reached an AUC of 0.838 (95% CI: 0.690-0.934) (FIG. 9).

IGFBP2 Levels and Correlations with Clinical Parameters

Univariate analysis of correlation between IGFBP2 and BNP with main characteristics parameter of the patients are reported in Table 4. IGFBP2 and BNP levels were strongly correlated together (rho=0.722; p<0.001). Furthermore BNP and IGFBP2 levels were similarly correlated to diuretic and C reactive protein, creatinine clearance and LVEF.

External Validation of IGFBP2 as a AHF Biomarker

We tested the predicting value of IGFBP2 for AHF diagnosis on a cohort of patients recruited at Paris Lariboisière Hospital. This cohort comprised AHF and COPD patients and is described in Table 5. Use of the threshold 556 ng/ml which was previously and independently determined in the discovery-validation cohort as indicated above led to a sensitivity of 80% for AHF diagnostic and a specificity of 90% for COPD patients (data not shown).

Example 3: Animal Analysis

Material & Methods

Rats HF Model and Transthoracic Echocardiography

The investigation conformed to the National Institutes of Health Guide for Care and Use of Laboratory Animals was allowed by the Inserm Animal Ethics Committee. The study, using myocardial infarction in 2 month old Sprague-Dawley rats (Janvier labs) by coronary artery ligation, was approved by the Local Animal Ethics Committee (#MP/03/03/01/12). Transthoracic echocardiographic analyses were performed for left ventricular ejection fraction measurement using the Vivid 7 pro 7 echocardiographic system (GE Medical System) as already performed.

Results

Test of IGFBP2 in a Rat Model of Ischemic HF

At day 20, i.e 4 days after surgery induced ischemia, the animals had a lowered ejection fraction (FIG. 10A) until day 70 when animals were euthanatized and the organs collected. Analysis of the gene expression levels in tissues showed that IGFBP2 mRNA levels were increased in the ischemic animals atria compared with sham-operated (FIG. 10B). Interestingly and at this time point, atria IGFBP2 mRNA levels from HF animals were ten times higher vs ventricle and 4 times increased vs liver.

Discussion

Plasma BNP or NT-proBNP levels are valuable tools to diagnose patients with HF 2. Therefore, we compared both IGFBP2 diagnostic value to the one of BNP and the putative added value of IGFBP2 to BNP. The diagnostic performance of IGFBP2 measurement led us to discriminate HF cases from control cases without heart disease (CRF and NCD patients) with an increased AUC compared to the one of BNP. Logistic combination of IGFBP2 and BNP led to an increased AUC compared to BNP alone when testing the use of IGFBP2 and BNP in the discrimination between NCD and AHF patients. The added value of IGFBP2 diagnostic performance was even more evident in patients with moderate BNP elevation i.e. in the 100-600 pg/ml concentration range.

IGFBP2 up-regulation point out a potential role for Insulin-like growth factor (IGF)-binding proteins (IGFBPs) in HF and more largely involves the somatotrope axis that encompass hypothalamic hormones such as hypothalamic Growth-hormone-releasing-hormone (GHRH), hypohyse Growth-hormone and IGF 1 and 2. IGFBPs confer regulation to IGF bioactivity but can also have a direct role. Clearly, IGF1's availability is regulated by Insulin Growth Factor Binding Protein IGFBPs. Only one to 5% of IGF1 is free in the blood stream, the remaining IGF1 is tightly bound to IGFBPs with an affinity that is greater or equal to the one for its receptor. Thus, IGFBPs modulate IGF1 and IGF1 receptor interaction. However, some IGFBPs were recently found to have their own activity even in the absence of IGF, through a direct interaction with transcription factors and modulation of gene expression.

IGFBP2 is the second most abundant IGFBP in human plasma. IGFBP2 is mostly an IGF1 inhibitor. Our correlation data confirmed that BNP and IGFBP2 plasma levels are not dependant on sex but are positively increased with age and negatively with the body mass index.

IGF1 was recognized to be involved in growth and myocardial development 28. IGF1 and it receptor are expressed in heart since the faetal stage and induce mycocardial hypertrophy through MAP-Kinases and PI-3 kinase pathways. IGF1 also stimulates myocardial protein production, including some with contractile functions such as troponine and actin. Therefore, IGF1 relates to cardiac contractile function and IGF1 levels are correlated to the left ventricular ejection fraction (LVEF). IGF1 is also involved in cardiomyocytes survival and apoptosis. Murine models and also small clinical trials involving GH or IGF1 injection have revealed a reduction of heart early remodeling, an improvement of the systolic and diastolic function, and a contractility improvement. Recently, the addition of the neutralising IGFBP2 antibody upon cell differentiation, led to an important myoblasts hypertrophy.

This study allowed us to analyze the link between HF and plasma IGFBP2 and the potential use of IGFBP2 as a new biomarker. We clearly observed close to a 7-fold rise in IGFBP2 plasmatic concentration in HF patients. Moreover, the test of IGFBP2 in the BNP "grey zone" revealed increased discriminating power for this new biomarker.

IGFBP2 is mainly produced by the liver and the heart therefore is likely to be indicative of liver or heart function. These points were evaluated in the ischemic rat model of HF which also revealed a stronger IGFBP2 mRNA level in atria vs ventricle or liver. Above all, IGFBP2 mRNA levels were significantly increased in the atria from HF animals. This observation raises the question of the putative role of IGFBP2 in atria. One could speculate that IGFP2 increased synthesis could be involved in a protective mechanism against excessive remodeling in heart because reduction in vitro antibodies based neutralization of IGFBP2 upon myoblasts differentiation led to hypertrophy 34. In addition, overexpression of IGFBP2 led to a reduction in muscle mass in the mouse 36. However, despite solid backgrounds, this hypothesis will have to be further tested in animals' models of HF.

Finally, we observed a significant negative correlation of the IGFBP2 level with the LVEF value in patients. These observations tend to propose the use of IGFBP2 as a potential follow-up biomarker that could be used to estimate the stability and heart failure severity. However, because of its sensitivity and specificity in HF, the first use of IGFBP2 could be in complementation with BNP in HF diagnosis in a population of patients with acute dyspnea form cardiac origin or not.

This study suffers from some limitations. The validation of the new IGFBP2 biomaker was performed with a small external cohort of patients. However, the rise of IGFBP2 concentration in AHF patients was reliable and qualifies IGFBP2 as a new biomarker. We now aim at testing IGFBP2 in very large multicentric international cohorts for further validations. Furthermore, the functional role of IGFBP2 in HF will be defined in rodent animal models.

The use of IGFBP2 as HF biomarker is promising and may improve HF diagnostic especially in the BNP range of values indicative of mild to moderate HF. Despite IGFBP2 synthesis is mainly produced by the heart, it is also secreted by the liver. This observation should not impair the use of IGFBP2 for HF diagnosis. Clearly, HF is a syndrome and our data propose that IGFBP2 is a reliable biomarker that could reveal the heart functional status.

REFERENCES

Throughout this application, various references describe the state of the art to which this invention pertains. The disclosures of these references are hereby incorporated by reference into the present disclosure.

Delahaye, F., Roth, O., Aupetit, J. F. & de Gevigney, G. [Epidemiology and prognosis of cardiac insufficiency]. Arch Mal Coeur Vaiss 94, 1393-1403 (2001).

Harmancey R, Senard J-M, Rouet P, Pathak A, Smih F. Adrenomedullin inhibits adipogenesis under transcriptional control of insulin. Diabetes. 2007; 56:553-63.

Hassfeld S, Eichhorn C, Stehr K, Naegele H, Geier C, Steeg M, Ranke M B, Oezcelik C, Osterziel K J. Insulin-like growth factor-binding proteins 2 and 3 are independent predictors of a poor prognosis in patients with dilated cardiomyopathy. Heart. 2007 March; 93(3):359-60.

Mischak, H. et al. Comprehensive human urine standards for comparability and standardization in clinical proteome analysis. Proteomics Clin Appl 4, 464-478, doi:10.1002/prca.200900189 (2010).

Phillips K, M A Park, L H Quarrie, M Boutinaud, J D Lochrie, D J Flint, G J Allan, J Beattie. Hormonal control of IGF-binding protein (IGFBP)-5 and IGFBP-2 secretion during differentiation of the HC11 mouse mammary epithelial cell line. Journal of molecular endocrinology, 31:197-208 (2003).

The invention claimed is:

1. A method of treating heart failure in a patient in need thereof, comprising the steps of:
    a) obtaining a biological sample from said patient;
    b) measuring the concentration of IGFBP2 in the sample obtained in step a);
    c) determining the severity of the heart failure depending on the concentration of IGFBP2 measured in step b); and
    d) administering to said patient diagnosed as having heart failure an appropriate medication for a subject suffering from heart failure depending on the severity of the heart failure as determined in step c).

2. The method according to claim 1, wherein the severity of the heart failure depending on the concentration of IGFBP2 measured in step b) is determined according to the NYHA heart failure classification.

3. The method according to claim 1, wherein step b) is performed by measuring the level of IGFBP2 protein in the sample obtained in step a).

4. The method according to claim 1, wherein the biological sample obtained in step a) is a urine sample.

5. The method according to claim 1, wherein the biological sample obtained in step a) is a plasma sample.

6. The method according to claim 1, wherein the biological sample obtained in step a) is a serum sample.

7. The method according to claim 1, wherein the measuring of the concentration of IGFBP2 is performed by using a set of antibodies direct against IGFBP2.

8. The method according to claim 5, wherein measuring the level of IGFBP2 protein is performed by ELISA.

* * * * *